United States Patent [19]

Green et al.

[11] 4,035,480

[45] July 12, 1977

[54] MICROBIOCIDAL MIXTURES OF POLYMERIC QUATERNARY AMMONIUM COMPOUNDS

[75] Inventors: Harold A. Green, Havertown, Pa.; John J. Merianos, Jersey City; Alfonso N. Petrocci, Glen Rock, both of N.J.

[73] Assignee: Millmaster Onyx Corporation, New York, N.Y.

[21] Appl. No.: 666,789

[22] Filed: Mar. 15, 1976

Related U.S. Application Data

[63] Continuation-in-part of Ser. No. 486,960, July 10, 1974, abandoned, which is a continuation-in-part of Ser. No. 425,931, Dec. 18, 1973, Pat. No. 3,874,870.

[51] Int. Cl.² ............... A61K 31/74; A01N 9/00; A01N 9/22
[52] U.S. Cl. ............... 424/78; 424/248.4; 424/267; 424/274; 424/329
[58] Field of Search ............... 424/78, 325, 329; 260/87.5 R; 71/67

[56] References Cited

U.S. PATENT DOCUMENTS

| | | | |
|---|---|---|---|
| 3,140,976 | 7/1964 | Berenschot et al. | 424/329 |
| 3,539,684 | 11/1970 | Hoover | 424/78 |
| 3,771,989 | 11/1973 | Pera et al. | 424/329 |
| 3,778,283 | 12/1973 | Freyhold | 106/84 |

FOREIGN PATENT DOCUMENTS

69-8949   7/1970   South Africa

*Primary Examiner*—Albert T. Meyers
*Assistant Examiner*—D. W. Robinson
*Attorney, Agent, or Firm*—Arthur A. Jacobs

[57] ABSTRACT

Bactericidal products comprising mixtures of polymeric quaternary ammonium compounds which are the condensation products of 1,4-dihalo-2-butene and a difunctional tertiary amine of the type

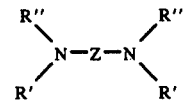

wherein Z consists of from one to three aliphatic radicals of 2 to 10 carbon atoms, each aliphatic radical containing 0 to 2 double bonds and 0 to 2 hydroxy substituents; and wherein R' and R" may be either the same or different and may be either (a) primary or secondary alkyls having from 1 to 20 carbon atoms with a total sum of no greater than 36 carbon atoms, (b) hydroxy or dihydroxy derivatives of the aforesaid primary or secondary alkyls, (c) benzyl, (d) alkyl-benzyl, or (e) combined with N to form a heterocyclic group of either 5, 6 or 7 atoms.

8 Claims, No Drawings

MICROBIOCIDAL MIXTURES OF POLYMERIC QUATERNARY AMMONIUM COMPOUNDS

This is a continuation-in-part of co-pending application Ser. No. 486,960, filed July 10, 1974 now abandoned, which is a continuation-in-part of application Ser. No. 425,931, filed Dec. 18, 1973, and issued as U.S. Pat. No. 3,874,870 on Apr. 1, 1975.

As set forth in the aforesaid parent applications, it was discovered that the condensation products of 1,4-dihalo-2-butene and 1,4-bis-dimethylamino-2-butene were highly effective microbiocidal agents in aqueous systems, particularly in recirculating and industrial waters as well as in emulsions containing non-ionic emulsifiers, and that the microbiocidal action was effected without undue foaming. A particular aspect of such compounds is that the quaternary ammonium moieties thereof are part of a long chain rather than part of a shorter chain bonded to the long chain.

It has now been discovered, in accordance with the present invention, that similar biocidal activity is obtained with mixtures of such compounds prepared as the condensation products of 1,4-di-halo-2-butene and certain diamines, more particularly, difunctional tertiary amines of the type:

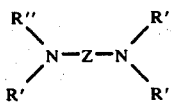

wherein Z consists of from one to three divalent aliphatic radicals of 2 to 10 carbon atoms which may contain 0 to 2 double bonds or 0 to 2 hydroxy substituents; wherein R' and R'' are either the same or different and wherein they may be: (a) primary or secondary alkyls having from 1 to 20 carbon atoms, where the sum of the carbon atoms in R' and R'' is no greater than 36 and where such sum is at least 3 when Z is —$CH_2$—CH=CH—$CH_2$—, (b) hydroxy or dihydroxy derivatives of the primary or secondary alkyl radicals described in (a), (c) benzyl, (d) benzyl having at least one alkyl group attached to the benzene ring, where the total number of carbon atoms in the alkyl groups attached to the benzene ring is less than 7, or (e) combined with N to form a heterocyclic group of either 5, 6 or 7 atoms. Exemplary of such heterocyclic groups are N-piperidino, N-pyrolidino, N-morpholino or N-homopiperidino.

Exemplary of difunctional tertiary amines themselves are N,N'-di-lower alkyl piperazine and 1,4-diazabicyclo (2.2.2) octane, as well as others hereinafter disclosed.

The condensation products of this invention are formed by mixing the butene and the amine, with agitation, at a temperature of between about 50° C to about 70° C, and then agitating the mixture at a temperature at least as high as the temperature maintained during the initial mixing until the reaction is complete, the butene and amine being in a molar proportion of between about 3:2 and about 2:3.

There is no absolute certainty of the actual structure of the product of the condensation reaction because of possible isomerizations; however, ideally, the reaction would appear to be exemplified by the following, wherein Z, R' and R'' are the same as in the formula above, wherein X is a halogen such as chlorine or bromine, and wherein n is an integer of from about 2 to about 30:

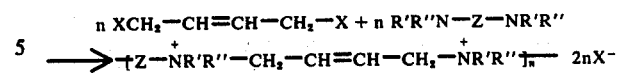

When Z is the divalent organic radical —$CH_2$—CH=CH—$CH_2$—, the reaction may be presented as follows:

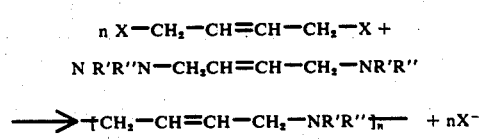

where the meaning of each symbol is the same as that described above.

Although some of the aforesaid compounds are active against Pseudomonas aeruginosa and Aerobacter aerogenes at a concentration as low as 25 ppm, relative to total composition, the preferred range is about 50-100 ppm. Insofar as concerns the upper limits, the concentration appears capable of being increased indefinitely without deleteriously affecting the biocidal activity.

With regard to cosmetic compositions, at least some of the products appear to be effective at a concentration as low as about 500 ppm, or probably even lower, although the preferred range is about 1,000 to about 2,000 ppm. Furthermore, when nonionic emulsifiers, such as are generally used is cosmetic compositions, are present, there appears to be no significant diminution of the biocidal effectiveness of these products. This is in contrast to the behavior of mono-quaternaries which lose their biocidal effectiveness is cosmetics that are emulsified with non-ionic emulsifiers.

There should be at least 10 percent of each polyquaternary compound relative to the total polyquaternary content in the mixture.

EXAMPLE 1

522 grams of morpholine (6 moles) were cooled to 20° C and 125 grams of 1,4-dichloro-2-butene (1 mole) were added dropwise with constant stirring and cooling to keep the temperature at 50° C – 60° C. The entire addition took about 1 hour, and stirring was continued for about 1 more hour. While stirring, 150 grams of water was poured into the reaction mixture, followed by 300 grams of 50% sodium hydroxide solution, then the mixture was allowed to separate.

The organic layer was removed, and the unreacted morpholine was removed by distillation under reduced pressure. The residue was washed with water and filtered, yielding a yellow solid melting at 79° – 83° C. This was 1,4-bis-(N-morpholino)-2-butene.

Since the purpose of the excess morpholine was to act as an acid acceptor, the experiment was repeated, but with 212 grams of sodium carbonate (2 moles) replacing the excess 174 grams of morpholine (4 moles). The yield of 1,4-bis-(N-morpholino)-2-butene was about the same as the previous synthesis.

This reaction was repeated using 0.1 mole of 1,4-dichloro-2-butene and 0.6 mole of the following amines in place of morpholine: piperidine, homopiperidine, diethanolamine, dimethylamine, dipropylamine, dibutylamine, di-(2-ethylhexyl) amine, dioctylamine, didecylamine, didodecylamine. N-methyl propylamine, N-methyl butylamine, N-methyl hexylamine, N-methyl octylamine, N-methyl decylamine, N-methyldodecylamine. All of these 1,4-bis-amino-2-butenes were liquids, and were recovered from their aqueous mixtures by partitioning.

EXAMPLE 2

22.6 grams of 1,4-bis-(N-morpholino)-2-butene (0.1 mole) was suspended in 25 grams of water, and to it was added dropwise, with constant stirring, 12.5 grams of 1,4-dichloro-2-butene (0.1 mole) at a rate which kept the reaction temperature between 60° and 70° C. The addition took about 15 – 30 minutes. Then the reaction mixture was stirred for about one hour on a steam bath at about 80° C at which time analyses for ionic chloride showed that the reaction was about 98 – 100% complete. The reaction product was a viscous material containing about 55% of active polyquaternary compound. When an excess of an organic solvent; i.e. an alcohol such as isopropanol or a ketone such as acetone, was added to the aqueous solution, the polyquaternary product precipitated and was separated by filtration.

Quite surprisingly, when organic solvents such as isopropanol, acetone, or inert halogenated solvent such as 1,1,1-trichloroethane were used instead of water as the reaction solvent, the polymeric quaternary product precipitated out of the reaction mixture as a solid, and was separated by filtration.

This same procedure was followed, using each of the other di-tertiary amines made in Example 1 instead of 1,4-bis-(N-morpholino)-2-butene.

In addition to the 1,4-ditertiary amino-2-butenes described in Example 2, other di-tertiary amines were reacted with 1,4-dichloro-2-butene to produce polyguaternary compounds, as shown by the following examples:

EXAMPLE 3

11.4 grams of -N,N'-dimethylpiperazine (0.1 mole) was suspended in 25 grams of water and to it was added dropwise, with constant stirring, 12.5 grams of 1,4-dichloro-2-butene (0.1 mole) at a rate which kept the reaction temperature between 60° and 70° C. The addition took about 15–30 minutes. Then the reaction mixture was stirred for about one hour on a steam bath at about 80° C at which time analysis for ionic chloride showed that the reaction was about 98   100% complete. The reaction product was a viscous material containing about 45% of active polyquaternary compound. When excess of a organic solvent such as isopropanol or acetone was added to the aqueous soluton, the polyquaternary product precipitated, and was separated by filtration.

Here, too, when organic solvents such as isopropanol, acetone, or 1,1,1-trichloroethane were used instead of water as the reaction solvent, the polymeric quaternary product precipitated out of the reaction mixture as a solid, and was separated by filtration.

EXAMPLE 4

The procedure of Example 3 was repeated using 0.1 mole of the following di-tertiary amines instead of N,N'-dimethyl piperazine: 1,4-diazabicyclo (2.2.2) octane; N,N',N'-tetramethyl ethylenediamine; N,N,N',N'-tetra-(2-hydroxypropyl) ethylenediamine; 1,3-bis-(dimethylamino)-2-hydroxypropane.

In order to test the biocidal and foaming properties of this inventions, the following representative products were chosen for each test:

a. The polyquaternary ammonium product formed by the condensation of 1,4-dichloro-2-butene with 1,4-diazabicyclo (2.2.2) octane in approximately equimolar proportions.

b. The polyquaternary ammonium product formed by the condensation of 1,4-bis-(N-morpholino)-2-butene with 1,4 dichloro-2-butene in approximately equimolar proportions.

c. The polyquaternary ammonium product formed by the condensation of 1,4-dichloro-2-butene with 1,4-di(N-homopiperidino)-2-butene in approximately equimolar proportions.

d. The polyquaternary ammonium product formed by the condensation of 1,4-dichloro-2-butene with 1,3-bis-(dimethylamino)-2-hydroxy propane in approximately equimolar proportions.

e. The polyquaternary ammonium product formed by the condensation of 1,4-dichloro-2-butene with N,N,N'N'-tetra(2-hydroxypropyl)-ethylene diamine in approximately equimolar proportions.

f. The polyquaternary ammonium compound formed by the condensation product of 1,4-dichloro-2-butene with N,N'-dimethylpiperazine in approximately equimolar proportions.

g. The polyquaternary ammonium compound formed by the condensation product of 1,4-dichloro-2-butene and 1,4-bis-dimethylamino-2-butene in equimolar proportions.

Two types of mixtures were prepared using the aforesaid compounds, one type being solid and the other liquid. These were prepared as follows:

The solid mixtures of this invention were prepared by weighing out two or more components comprising the mixture in the desired ratios by weight, then placing the components in a mortar, and stirring with a pestle until the mixture had the appearance of homogeneity.

The liquid mixtures were prepared by weighing the liquid components to achieve the desired ratios by weight of two or more polyquaternaries, and stirring with a pestle until the mixture had the appearance of homogeneity.

Although the mixtures may be made in any desired proportion of two or more of the compounds, the following are illustrative of such mixtures:

Mixture (1): Mixture of Compound (g) and Compound (a) in about 50:50 ratio by weight.

Mixture (2): Mixture of Compound (g) and Compound (a) in about 70:30 ratio by weight.

Mixture (3): Mixture of Compound (g) and Compound (b) in about 70:30 ratio by weight.

The broth dilution method was used to determine the minimum inhibitory level of the several representative mixtures of polymeric quaternary products against a variety of bacteria. The organisms chosen were *Escherichia coli, Pseudomonas aeruginosa, Staphylococcus aureus,* and *Streptococcus faecalis.*

A nutrient broth for testing *E. coli, P. aeruginosa,* and *S. aureus* was made up by dissolving:

5.0 grams of beef extract
5.0 grams of sodium chloride
10.0 grams of peptone per liter of solution.

The nutrient broth for testing *S. faecalis was made up by dissolving:*

2.5 grams of dextrose 5.0 grams of sodium chloride
2.5 grams of dipotassium phosphate
20.0 grams of peptone
per liter of water.

Each broth used for testing was sterilized for 15 minutes at 15 pounds of steam.

To 9.0 ml. of broth, 1.0 ml. of aqueous solution of each compound to be tested was added in appropriate concentrations to make the final mixture contain 500, 250, 100, 50, 25, ppm. Then 0.1 ml. of a 24-hour bacterial broth culture was added into each tube to give a final bacterial count of $(1-10) \times 10^6$ organisms per ml. of inoculated broth.

The tubes so inoculated were incubated at 37° C, and the results were recorded for turbidity growth after 48 and 96 hours.

The lowest concentration of experimental product being tested which did not permit microscopic growth of test bacteria was considered to be the minimum inhibitory level for that specific bacteria being tested.

The results of the tests, portraying the relationship between minimum inhibitory concentrations and test organisms, are shown in the following table:

Table 1

| Product | Minimum Inhibitory Concentration in ppm. Test Bacteria | | | |
|---|---|---|---|---|
| | E. coli | P. aeruginosa | S. aureus | S. Faecalis |
| Mixture (1) | 100 | 100 | 100 | 100 |
| Mixture (2) | 50 | 100 | 150 | 50 |
| Mixture (3) | 100 | 100 | 100 | 100 |

The tests clearly indicate that the mixtures of polyquaternaries are effective inhibitors of bacterial growth.

EXAMPLE 5

In order to test the foaming properties of mixtures of polyquaternary ammonium compounds, the extremely vigorous "Waring Blender Test" was used. The procedure for this test follows:

A graduated blender cylinder is rinsed with distilled water, and 100 ml. of aqueous test solution is added down the walls of the cylinder so as to cause no foam. The blender is turned on at high speed for exactly 5 seconds, and upon turning the blades off, timing is started with a stop watch, and at the same time the foam weight is read in mm. from the 100 ml. mark, and noted.

The foam half-life is defined and noted as the time it takes for the liquid to drain out of the foam and reach the 50 ml. mark.

The test results were as follows:

Table 2

Waring Blender Foam Test at 25° C., concentration 100 ppm.

| Compound | Distilled Water | | 300 ppm. in hard water | |
|---|---|---|---|---|
| | Foam Height (mm.) | Half-life (sec.) | Foam Height (mm.) | Half-life (sec.) |
| Mixture (1) | 0/0 | | 0/0 | |
| Mixture (2) | 0/0 | | 0/0 | |
| Mixture (3) | 0/0 | | 0/0 | |

The test results show that the mixtures of polyquaternary ammonium products are non-foaming in distilled water, and in hard water.

The invention claimed is:
1. A mixture of at least two polymeric quaternary ammonium compounds, each of which is a condensation product of 1,4-dihalo-2-butene and a difunctional tertiary amine of the type

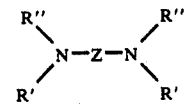

wherein Z consists of one to three alkylene groups of a total of 2 to 10 carbon atoms, each alkylene group containing 0 to 2 double bonds and 0 to 2 hydroxy substituents; and wherein R' and R" may be either the same or different and may be either (a) primary or secondary alkyls having from 1 to 20 carbon atoms with a total sum in both R' and R" of no greater than 36 carbon atoms, (b) hydroxy or dihydroxy derivatives of the aforesaid primary or secondary alkyls, (c) benzyl, (d) alkyl-benzyl, or (e) combined with N to form a heterocyclic moiety selected from the group consisting of N-piperidino, N-pyrolidino, N-morpholino, and N-homopiperidino, said condensation products being formed by mixing the butene and the amine, with agitation, at a temperature of between about 50° C to about 70° C and then agitating the mixture at a temperature at least as high as the temperature maintained during the initial mixing until the reaction is complete, the butene and amine being in a molar proportion of between about 3:2 and about 2:3.

2. The mixture of claim 1 wherein said alkyl-benzyl has at least one alkyl group attached to the benzene ring and where the total number of carbon atoms in such alkyl groups is less than 7.

3. The product of claim 1 wherein:

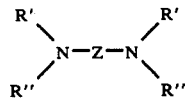

is a number of the group consisting of di-lower alkyl piperazine and 1,4-diazabicyclo (2.2.2) octane.

4. The mixture of claim 1 wherein at least one of the compounds of the mixture is selected from the group consisting of (a) the condensation product of 1,4-dichloro-2-butene with 1,4-diazabicyclo (2.2.2) octane; (b) the condensation product of 1,4-dichloro-2-butene with 1,4-bis-(N-morpholino)-2-butene; (c) the condensation product of 1,4-dichloro-2-butene with 1,4-di-(N-homopiperidine)-2-butene; (d) the condensation product of 1,4-dichloro-2-butene with 1,3-bis-(dimethylamino)-2-hydroxy propane; (e) the condensation product of 1,4-dichloro-2-butene with N,N,N'N'-tetra-(2-hydroxypropyl) - ethylene diamine; (f) the condensation product of 1,4-dichloro-2-butene with N,N'- dimethylpiperazine; and (g) the condensation product of 1,4-dichloro-2-butene and 1,4-bis-dimethylamine-2-butene.

5. A method of inhibiting bacteria which comprises applying to said bacteria an effective amount of the mixture of claim 1 sufficient to inhibit the growth of said bacteria.

6. A method of inhibiting bacteria which comprises applying to said bacteria an effective amount of the mixture of claim 2 sufficient to inhibit the growth of said bacteria.

7. A method of inhibiting bacteria which comprises applying to said bacteria an effective amount of the mixture of claim 3 sufficient to inhibit the growth of said bacteria.

8. A method of inhibiting bacteria which comprises applying to said bacteria an effective amount of the mixture of claim 4 sufficient to inhibit the growth of said bacteria.

* * * * *